(12) United States Patent
Leube et al.

(10) Patent No.: US 6,437,172 B1
(45) Date of Patent: Aug. 20, 2002

(54) PREPARATION OF (METH) ACRYLATES

(75) Inventors: Hartmann F. Leube, Ludwigshafen;
Kurt Leidinger, Limburgerhof;
Matthias Geisendörfer, Neustadt;
Erich Beck, Ladenburg, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/644,824

(22) Filed: Aug. 24, 2000

(30) Foreign Application Priority Data

Aug. 30, 1999 (DE) .......................................... 199 41 136

(51) Int. Cl.⁷ ............................................. C07C 69/52
(52) U.S. Cl. ....................................... 560/205; 560/224
(58) Field of Search .................................. 560/224, 205

(56) References Cited

U.S. PATENT DOCUMENTS

| 5,096,938 A | 3/1992 | Beck et al. |
| 5,498,751 A | 3/1996 | Trapasso et al. |

FOREIGN PATENT DOCUMENTS

| DE | 33 16 593 | 11/1984 |
| DE | 37 04 098 | 8/1988 |
| DE | 38 36 370 | 5/1990 |
| EP | 0 646 567 | 4/1995 |
| EP | 0 989 108 | 3/2000 |
| JP | 363122649 | * 5/1988 |
| JP | 94037425 | * 5/1994 |

* cited by examiner

*Primary Examiner*—Paul J. Killos
(74) *Attorney, Agent, or Firm*—Oblon, Spivak, McClelland, Maier & Neustadt, P.C.

(57) ABSTRACT

(Meth)acrylates are prepared by esterifying a high-boiling compound having one or more alcoholic hydroxyl groups with (meth)acrylic acid in the presence of an entraining agent, such as a (cyclo)aliphatic hydrocarbon, by heating the reaction mixture to the boil and discharging the water of reaction with the entraining agent, in a substantially shorter reaction time and constant product quality, if, during the esterification reaction, the entraining agent is metered into the reaction mixture under temperature control at a rate such that the boiling point of the reaction mixture remains constant.

15 Claims, No Drawings

PREPARATION OF (METH) ACRYLATES

The present invention relates to an improved process for the preparation of (meth)acrylates by esterifying a high-boiling compound having one or more alcoholic hydroxyl groups with (meth)acrylic acid in the presence of an acidic esterification catalyst and of an entraining agent with discharge of the water of reaction and temperature-controlled recycling of the entraining agent into the reaction mixture.

The esterification of high-boiling compounds having aliphatic hydroxyl groups with (meth)acrylic acid has become very important industrially owing to the wide use of esterification products for radiation-curable finishes and coatings. For this purpose, hydroxy compound, (meth) acrylic acid, catalyst, stabilizer and entraining agent are initially taken in the batch process. After heating to the boil, the water of reaction formed during the esterification reaction is distilled off as an azeotropic mixture comprising entraining agent and water. The azeotropic mixture distilled off is condensed and is separated into water and entraining agent in a downstream phase separator. The entraining agent separated off is then recycled directly to the reaction vessel to remove further water of reaction. After the end of the esterification reaction and the end of removal of liberated water of reaction, all the entraining agent is removed from the reaction mixture by distilling off (cf. for example DE-A-3316593, DE-A-3704098, DE-A-3836370, EP-A-646567). In the conventional esterification process, the boiling point corresponds to the reaction temperature and, as a result of the method of water removal, the content of entraining agent in the reaction mixture is constant.

It has long been desired to reduce the long duration of the esterification equilibrium reaction. An increase in the reaction rate can be achieved, for example, by increasing the reaction temperature, which however increases the danger of polymerization of the unsaturated monomers during the esterification reaction. It must also be borne in mind that most of the conventional stabilizer systems readily lead to discoloration of the product at high esterification temperatures. This limits the choice of high esterification temperatures because resulting discolorations can be eliminated only by tedious measures such as distillation, washing out, etc. For example, in the case of the otherwise advantageous inhibitor system comprising copper(II) chloride and hydroquinone monomethyl ether, an esterification temperature of about 105° C. should therefore not be exceeded in order to obtain high-quality colorless products.

The temperature of the reaction mixture is a function of the boiling point of the entraining agent used. High-boiling entraining agents, such as toluene, have the advantage that they have a good entraining effect for water and lead to relatively high boiling points of the mixture, with the result that the esterification range can be increased. The disadvantage is that the high-boiling entraining agents are difficult to separate from some end products. In addition, they must be used in high concentrations since otherwise the resulting boiling point of the mixture will be too high and there is a danger of polymerization. Low-boiling entraining agents, e.g. cyclohexane, have the disadvantage of too low an entraining effect and a reduction in the reaction temperature and hence in the reaction rates. However, they have the advantage that they can be used in lower concentrations and can be more easily removed after the end of the reaction.

However, the boiling point of the reaction mixture is also a function of the composition of the mixture. Since the composition of the mixture changes during the reaction as a result of the reaction of hydroxy compound and acid to form the ester, the reaction temperature also increases during the esterification. With a constant amount of an entraining agent it is necessary to carry out the esterification reaction initially at low temperatures and at a low reaction rate in order to avoid reaching, at the end of the reaction, a temperature at which there is a danger of polymerization. Consequently, esterification times which are undesirably long for economic reasons result.

In principle, it is possible to regulate the boiling point by controlling the pressure, but this requires working in special expensive pressure-resistant apparatuses.

It is an object of the present invention to provide a process for the preparation of esters of (meth)acrylic acid with high-boiling alcohol compounds, in which a good constant product quality is achieved in combination with a very uniform optimum reaction temperature. It is a further object of the invention to achieve an increase in the reaction rate and hence a reduction in the reaction time in the esterification reaction.

We have found that this object is achieved by a process for the preparation of (meth)acrylates by esterifying a high-boiling compound having one or more alcoholic hydroxyl groups with (meth)acrylic acid in the presence of an acidic esterification catalyst, of an entraining agent for the water of reaction and of a polymerization inhibitor while heating the reaction mixture to the boil and discharging the water of reaction with the aid of the entraining agent and feeding entraining agent to the reaction mixture during the esterification reaction, wherein the entraining agent is metered batchwise into the reaction mixture under temperature control during the predominant duration of the esterification reaction so that the boiling point of the reaction mixture is kept essentially constant, essentially within a range of ±2° C.

In the novel process, the usual inevitable recycling of entraining agent from the phase separator in the removal procedure is therefore omitted. Instead, the entraining agent is metered into the reaction mixture under temperature control or under control by the respective temperature of the reaction mixture in such a way that, through the boiling point of the reaction mixture, a constant internal temperature of the reaction mixture results during the predominant duration (in particular during more than 70%, preferably more than 80% or 90% of the total duration) and preferably during the essentially total duration of the esterification reaction. Preferably, the variations in the boiling points, apart from initial settling variations, should be no greater than ±2° C. In this way, the procedure can be carried out at a constant optimum reaction temperature during the total esterification reaction, which, as stated, leads to constantly good product quality and to a reduction in the reaction times of the esterification.

Preferably, the boiling point of the reaction mixture, including entraining agent, is from 70 to 110° C., particularly preferably from 75 to 105° C., low-boiling entraining agents being used. The boiling point of the reaction mixture is preferably more than 5° C., in particular more than 10° C., higher than the boiling point of the pure entraining agent (at the same pressure).

A further advantage of the novel process is that the reaction kettle for the esterification reaction can be filled to a higher level with the reaction mixture from the outset, since less volume is required for the entraining agent at the beginning of the esterification reaction. If the volume of the reaction mixture decreases owing to discharged water of reaction, further entraining agent is metered in.

Particularly suitable entraining agents are aliphatic and cycloaliphatic saturated hydrocarbons which are capable of forming an azeotropic mixture with water and have a boiling point of from 40 to 120° C., in particular from 70 to 110° C. Suitable low-boiling entraining agents are, for example, n-hexane, n-heptane, cyclohexane and methylcyclohexane, special gasolines and commercial aliphatic hydrocarbon mixtures having boiling points in the stated temperature ranges. A preferred entraining agent is cyclohexane. In general, the entraining agents are used in an amount of from 1 to 80, preferably from 1 to 35, % by weight, based on the sum of the amounts of hydroxy compound and (meth)acrylic acid.

Suitable compounds which have a high boiling point, i.e. at least higher than the boiling point of the entraining agent used, and have one or more alcoholic hydroxyl groups are in particular polyols having from 2 to 6 alcoholic hydroxyl groups, in addition to high-boiling monohydric alcohols such as lauryl alcohol or 2-ethylhexyl alcohol. Examples of polyols having alcoholic hydroxyl groups which have in particular 2 to 20 carbon atoms are ethylene glycol, propylene glycol, 1,2-, 1,3- and 1,4-butanediol, neopentyl glycol, 1,5-pentanediol, 1,6-hexanediol, glycerol, trimethylolethane, trimethylolpropane, ditrimethylolpropane, sorbitol, pentaerythritol and dipentaerythritol. Other very suitable components having alcoholic hydroxyl groups are oligomers of $C_2$–$C_4$-alkylene glycols which contain in particular from 2 to 4 alkylene glycol units in the molecule, e.g. diethylene glycol, triethylene glycol, dipropylene glycol or tripropylene glycol. very suitable hydroxy compounds for the novel esterification are also alkoxylation products of alcohols and in particular ethoxylated and/or propoxylated polyhydric alcohols, such as ethoxylated trimethylolpropane, ethoxylated and/or propoxylated pentaerythritol. In general, such alkoxylated products contain from 1 to 20, preferably from 1 to 10, alkoxy groups per polyol molecule. Other polyols which may be used, in addition to polyetherpolyols, are polyesterpolyols, ether-modified polyesterpolyols, polyepoxide resins having a plurality of aliphatic hydroxyl groups or corresponding polyurethanes. Liquid to viscous low molecular weight and oligomeric compounds having alcoholic hydroxyl groups are preferred for the esterification.

Acids used for the esterification are methacrylic acid, acrylic acid or mixtures of these acids, a preferred acid being acrylic acid.

For the esterification reaction, components containing acid and hydroxyl groups are used in particular in amounts of from 1 to 1.5 mol of (meth)acrylic acid per hydroxyl group of the mono- or polyol component. However, the amount of acid can also be correspondingly reduced if only some of the hydroxyl groups of the polyol are to be converted into acrylates and/or methacrylates.

Suitable acidic esterification catalysts are strong organic or inorganic acids, which are generally used in amounts of from 0.1 to 5% by weight, based on the sum of the amounts of alcohol and (meth)acrylic acid component. Preferred acidic esterification catalysts are sulfuric acid, p-toluenesulfonic acid, methanesulfonic acid and strongly acid ion exchangers.

In order to avoid polymerization of unsaturated monomers, the esterification of the hydroxy compound with (meth)acrylic acid is carried out in the presence of small amounts of polymerization inhibitors. These are known organic and/or inorganic compounds used for preventing thermal polymerization, e.g. hydroquinone, hydroquinone monoalkyl ethers, 2,6-di-tert-butylphenol, nitrosamines, phenothiazine, copper compounds, such as copper(II) chloride, or combinations of such compounds. The polymerization inhibitors are added to the esterification mixture in conventional amounts, in general in amounts of from 0.001 to 5, in particular from 0.005 to 1, % by weight, based on the sum of the amounts of hydroxy compound and (meth)acrylic acid.

It has proven advantageous also to add color stabilizers, such as hypophosphorous acid ($H_3PO_2$), triphenyl phosphite or an organophosphonic acid, such as 1-hydroxyethane-1, 1-diphosphonic acid, to the esterification mixture before the esterification reaction, the amount of these additives being in general from 0.01 to 3% by weight, based on the sum of the amounts of the hydroxy and (meth)acrylic acid component.

After the end of the esterification reaction, in which a degree of esterification of at least 85, in particular from 90 to 95, % is to be achieved, the measures known per se or conventional measures for further working-up of the reaction products can be carried out. Thus, the entraining agent and any excess (meth)acrylic acid can then be distilled off, preferably at from 100 to 120° C. at from 10 to 150 mbar. The acidic esterification catalysts can be neutralized, added inhibitors or stabilizers can be washed out or precipitated and final amounts of (meth)acrylic acid can be reacted with epoxides in the presence of suitable catalysts. The present invention relates to the phase of the esterification reaction of the hydroxy component with (meth)acrylic acid and thus in no way limits the suitable working-up, known to those skilled in the art, of the resulting esterification products by known or conventional measures.

The examples which follow illustrate the present invention but are not restrictive.

EXAMPLE 1

Comparative Experiment 2832 g of propoxylated trimethylolpropane (3 mol of propylene oxide per mole of trimethylolpropane), 2249 g of acrylic acid, 221 g of a 65% strength by weight aqueous solution of p-toluenesulfonic acid as an esterification catalyst, 1663 g of cyclohexane as an entraining agent, 1.2 g of copper(II) chloride and 1 g of hydroquinone monomethyl ether as inhibitors were initially taken in a 7 liter stirred glass vesel with attached condenser, downstream condenser and phase separation vessel. The reaction mixture was heated to the boil and the resulting vapor mixture was completely condensed in the condenser and downstream condenser made of glass. A phase separation was then carried out in the phase separation vessel. The water of reaction formed in the esterification reaction was removed and the amount thereof formed was measured hourly. At the same time, the resulting internal temperature of the reaction mixture (Ti) was also measured hourly.

The cyclohexane separated off in the phase separation vessel was recycled as an entraining agent directly to the stirred vessel containing the reaction mixture, by a conventional procedure (continuous circulation of the entraining agent present in the batch). The reaction was continued until no more water separated off in the phase separation vessel. The resulting progress of the esterification reaction was determined on the basis of the amount of water of reaction separated off. The internal temperatures of the reaction mixture (Ti) measured hourly and the amounts of water of reaction ($H_2O$) obtained are shown in Table 1. With increasing reaction temperatures (from 78 to 94° C.) 652 g of water of reaction were separated off after 13 hours and 634 g after 11 hours.

TABLE 1

Example 1 (comparative experiment) - amounts of water of reaction ($H_2O$) and internal reactor temperatures (Ti) measured hourly

| | Time (h) | | | | | | | | | | | | | |
|---|---|---|---|---|---|---|---|---|---|---|---|---|---|---|
| | 0 | 1 | 2 | 3 | 4 | 5 | 6 | 7 | 8 | 9 | 10 | 11 | 12 | 13 |
| $H_2O$ (g) | 0 | 72 | 233 | 386 | 454 | 523 | 576 | 589 | 600 | 602 | 616 | 634 | 645 | 652 |
| Ti (°C.) | 78 | 79 | 81 | 86 | 88 | 89 | 91 | 92 | 92 | 92 | 93 | 93 | 94 | 94 |

EXAMPLE 2

According to the Invention

The procedure was as in Example 1, except that the condensed cyclohexane, as entraining agent, was not recycled directly from the phase separation vessel into the stirred reaction vessel but was transferred to a storage vessel. Cyclohexane was metered separately into the stirred reaction vessel in the amounts required for maintaining the desired internal temperature of the reaction mixture of 95° C. during the esterification reaction. The internal temperature (Ti) of the reaction mixture, measured hourly, and the amounts of water of reaction ($H_2O$) obtained are shown in Table 2. It was found that, at a constant temperature of the reaction mixture of from 94 to 95° C., 634 g of water of reaction had separated off after only 7 hours, i.e. the esterification reaction took place substantially more rapidly than in Example 1 using the conventional procedure.

TABLE 2

Example 2 (according to the invention) - amounts of water of reaction ($H_2O$) and internal temperatures of the reaction mixture (Ti) measured hourly

| | Time (h) | | | | | | | |
|---|---|---|---|---|---|---|---|---|
| | 0 | 1 | 2 | 3 | 4 | 5 | 6 | 7 |
| $H_2O$ (g) | 0 | 324 | 492 | 598 | 625 | 629 | 629 | 634 |
| Ti (°C.) | 95 | 94 | 95 | 95 | 95 | 95 | 95 | 95 |

EXAMPLE 3

Comparative Experiment 2077 g of 1,6-hexanediol, 3148 g of acrylic acid, 120 g of a 65% strength by weight aqueous solution of p-toluenesulfonic acid as esterification catalyst, 1614 g of cyclohexane as an entraining agent, 1.2 g of copper(II) chloride and 1.5 g of hydroquinone monomethyl ether as inhibitors were initially taken in a 7 l stirred glass vessel. The procedure was then continued as stated in Example 1, i.e. the cyclohexane separated off in the phase separation vessel was recycled as entraining agent directly into the stirred vessel containing the reaction mixture, by the conventional procedure. The internal temperatures of the reaction mixture (Ti) measured hourly and the amounts of water of reaction ($H_2O$) separated off are shown in Table 3. At an internal temperature of the reaction mixture Ti increasing from 78 to 101° C., 730 g of water of reaction were separated off after 8 hours.

TABLE 3

Example 3 (comparative experiment) - amounts of water of reaction ($H_2O$) and internal temperature of the reaction mixture (Ti) measured hourly

| | Time (h) | | | | | | | | |
|---|---|---|---|---|---|---|---|---|---|
| | 0 | 1 | 2 | 3 | 4 | 5 | 6 | 7 | 8 |
| $H_2O$ (g) | 0 | 173 | 391 | 484 | 489 | 597 | 721 | 728 | 730 |
| Ti (°C.) | 78 | 80 | 84 | 89 | 96 | 100 | 101 | 101 | 101 |

EXAMPLE 4

According to the Invention

The initially taken reaction mixture corresponded to that stated in Example 3. However, the procedure was then as stated in Example 2, i.e. the condensed cyclohexane, as entraining agent, was not recycled directly from the phase separation vessel into the reaction vessel but was transferred to a storage vessel. Cyclohexane was metered separately into the reaction vessel in the amounts required for maintaining a chosen internal temperature of the reaction mixture during the substantial duration of the progressing esterification reaction. The internal temperatures of the reaction mixture (Ti) measured hourly and the resulting amounts of water of reaction ($H_2O$) separated off are shown in Table 4. It was found that, without any increase in internal temperatures 730 g of water of reaction had separated off after only 6 hours in the course of the esterification reaction, i.e. a more rapid esterification reaction could be achieved.

TABLE 4

Example 4 (according to the invention) - amounts of water of reaction ($H_2O$) and internal temperatures of the reaction mixture (Ti) measured hourly

| | Time (h) | | | | | | |
|---|---|---|---|---|---|---|---|
| | 0 | 1 | 2 | 3 | 4 | 5 | 6 |
| $H_2O$ (g) | 0 | 397 | 442 | 549 | 649 | 683 | 730 |
| Ti (°C.) | 78 | 101 | 97 | 95 | 95 | 95 | 95 |

We claim:

1. A process for the preparation of (meth)acrylates by esterifying a high-boiling compound having one or more alcoholic hydroxyl groups with (meth)acrylic acid in the presence of an acidic esterification catalyst, of an entraining agent for the water of reaction and of a polymerization inhibitor while heating the reaction mixture to the boil and discharging the water of reaction with the aid of the entraining agent and metering in entraining agent during the esterification reaction, wherein the entraining agent is metered into the reaction mixture under temperature control during the predominant duration of the esterification reaction so that the boiling point of the reaction mixture is kept essentially constant.

2. A process as claimed in claim 1, wherein the boiling point of the reaction mixture is from 70 to 110° C.

3. A process as claimed in claim 1, wherein the boiling point of the reaction mixture is from 75 to 105° C.

4. A process as claimed in claim 1, wherein the boiling point of the reaction mixture during the predominant duration of the esterification reaction is kept constant within ±2° C. by adding entraining agent.

5. A process as claimed in claim 1, wherein the entraining agent is a hydrocarbon having a boiling point of from 40 to 120° C.

6. A process as claimed in claim 1, wherein the entraining agent is cyclohexane.

7. A process as claimed in claim 1, wherein, in the esterification of the hydroxy compound with acrylic and/or methacrylic acid, the ratio of the number of equivalents of hydroxyl groups to that of carboxyl groups is from 1:1.0 to 1:1.5.

8. A process as claimed in claim 1, wherein an aliphatic or cycloaliphatic alcohol is used as the hydroxy compound to be esterified.

9. A process as claimed in claim 1, wherein an oligomer of ethylene glycol and/or propylene glycol is used as the hydroxy compound to be esterified.

10. A process as claimed in claim 1, wherein the boiling point of the reaction mixture is more than 5° C. higher than the boiling point of the pure entraining agent.

11. The process as claimed in claim 1, wherein said constant temperature is achieved during more than 70% of the duration of said esterification reaction.

12. The process as claimed in claim 1, wherein said constant temperature is achieved during more than 80% of the duration of said esterification reaction.

13. The process as claimed in claim 1, wherein said constant temperature is achieved during more than 90% of the duration of said esterification reaction.

14. The process as claimed in claim 1, wherein the boiling point of the reaction mixture is more than 10° C. higher than the boiling point of the pure entraining agent.

15. The process as claimed in claim 1, wherein an amount of said entraining agent is from 1 to 80% by weight based on the sum of the amounts of the compound having the alcoholic hydroxyl groups and (meth)acrylic acid.

* * * * *